United States Patent

Frazier et al.

(10) Patent No.: US 9,504,774 B2
(45) Date of Patent: Nov. 29, 2016

(54) INTRAATRIAL VENTRICULAR ASSIST DEVICE

(75) Inventors: Oscar H. Frazier, Houston, TX (US); William E. Cohn, Bellaire, TX (US)

(73) Assignee: MINVASC DEVICES, LLC, Houston, TX (US)

( * ) Notice: Subject to any disclaimer, the term of this patent is extended or adjusted under 35 U.S.C. 154(b) by 1443 days.

(21) Appl. No.: 12/243,256

(22) Filed: Oct. 1, 2008

(65) Prior Publication Data

US 2009/0088597 A1  Apr. 2, 2009

Related U.S. Application Data

(60) Provisional application No. 60/976,648, filed on Oct. 1, 2007.

(51) Int. Cl.
*A61M 1/12* (2006.01)
*A61M 1/10* (2006.01)

(52) U.S. Cl.
CPC .............. *A61M 1/101* (2013.01); *A61M 1/122* (2014.02); *A61M 1/125* (2014.02)

(58) Field of Classification Search
CPC .. A61M 1/122; A61M 1/1086; A61M 1/125; A61M 1/101
USPC ....................................... 600/16, 9
See application file for complete search history.

(56) References Cited

U.S. PATENT DOCUMENTS

| 4,995,857 | A | 2/1991 | Arnold |
| 6,942,611 | B2 * | 9/2005 | Siess ............................ 600/16 |
| 6,974,436 | B1 | 12/2005 | Aboul-Hosn et al. |
| 7,070,555 | B2 | 7/2006 | Siess |
| 7,125,376 | B2 | 10/2006 | Viole et al. |
| 7,229,402 | B2 | 6/2007 | Diaz et al. |
| 2005/0165344 | A1 | 7/2005 | Dobak, III |
| 2005/0187425 | A1 | 8/2005 | Alferness et al. |
| 2006/0155158 | A1 * | 7/2006 | Aboul-Hosn ......... A61M 1/101 600/16 |
| 2009/0149950 | A1 * | 6/2009 | Wampler ............... A61M 1/101 623/3.13 |
| 2009/0182188 | A1 * | 7/2009 | Marseille et al. .............. 600/16 |

FOREIGN PATENT DOCUMENTS

WO      2005037345 A2      4/2005

OTHER PUBLICATIONS

Written Opinion and Search Report dated Feb. 23, 2009 for International Application No. PCT/US2008/078435, 13 pages.
EPO Search Report dated Jun. 6, 2012, for EPO Application No. 08835735.5 (6 pgs.).

* cited by examiner

*Primary Examiner* — Michael Kahelin
*Assistant Examiner* — Minh Duc Pham
(74) *Attorney, Agent, or Firm* — Conley Rose, P.C.

(57) ABSTRACT

A medical device comprises a pump adapted to fit within an atrium of a heart, said pump comprising an inlet and an outlet. The device further comprises a flexible outflow conduit coupled to said outlet. A method of assisting ventricular function of a heart of a patient comprises: a) inserting a continuous flow pump having an inlet and an outlet into the heart via a subclavian or jugular vein; b) attaching the outlet of the continuous flow pump to an atrial septum, wherein the inlet of the continuous flow pump is directed into a heart atrium; c) attaching the distal end of the outflow conduit to an artery; and d) operating the pump at a volumetric rate ranging from about 2 L/min to about 3 L/min.

1 Claim, 5 Drawing Sheets

INTRAATRIAL VENTRICULAR ASSIST DEVICE

CROSS-REFERENCE TO RELATED APPLICATIONS

This application claims priority to U.S. Provisional Application Ser. No. 60/976,648 titled "Intraatrial Ventricular Assist Device" filed Oct. 1, 2007, incorporated herein by reference.

BACKGROUND

Over 50,000 people die each year because of congestive heart failure, a condition that often cannot be treated with drug or surgical therapies. Moreover, nearly 550,000 new patients are diagnosed with congestive heart failure each year. For many patients that suffer heart failure, an attractive option is heart transplantation. The scarcity of suitable donor hearts has limited the impact of this therapy, however. As such, recent efforts have focused on the development of mechanical pumps to assist the failing heart. Fortunately, great strides have been made in the development of ventricular assist devices ("VADs"). Instead of totally replacing heart function, a VAD augments the existing heart's ability to pump blood. These devices have saved many patients who would not have survived without a heart transplant. Despite it success, current VAD technology still has much room for improvement. Specifically, there is a need for less invasive methods and devices that may be used to temporarily or permanently assist a failing human heart.

BRIEF SUMMARY

Novel methods and devices for assisting ventricular function of a heart are described herein. Embodiments of the device may be implanted within the atrium of a heart and comprises an outflow conduit that passes through the atrial septum. The outflow conduit may then pass through the superior vena cava, out the subclavian vein and be attached to a subclavian artery. Alternatively, the device may be placed down the jugular vein. The disclosed device foregoes the need for a pocket outside of the heart and further does not entail cutting a hole in the ventricle. Minimally invasive surgical techniques may be employed to implant embodiments of the device. Other aspects and features of the disclosed methods and devices will be described in more detail below.

Thus, embodiments of the invention comprise a combination of features and advantages that enable it to overcome the problems of prior devices. The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Figure 1:
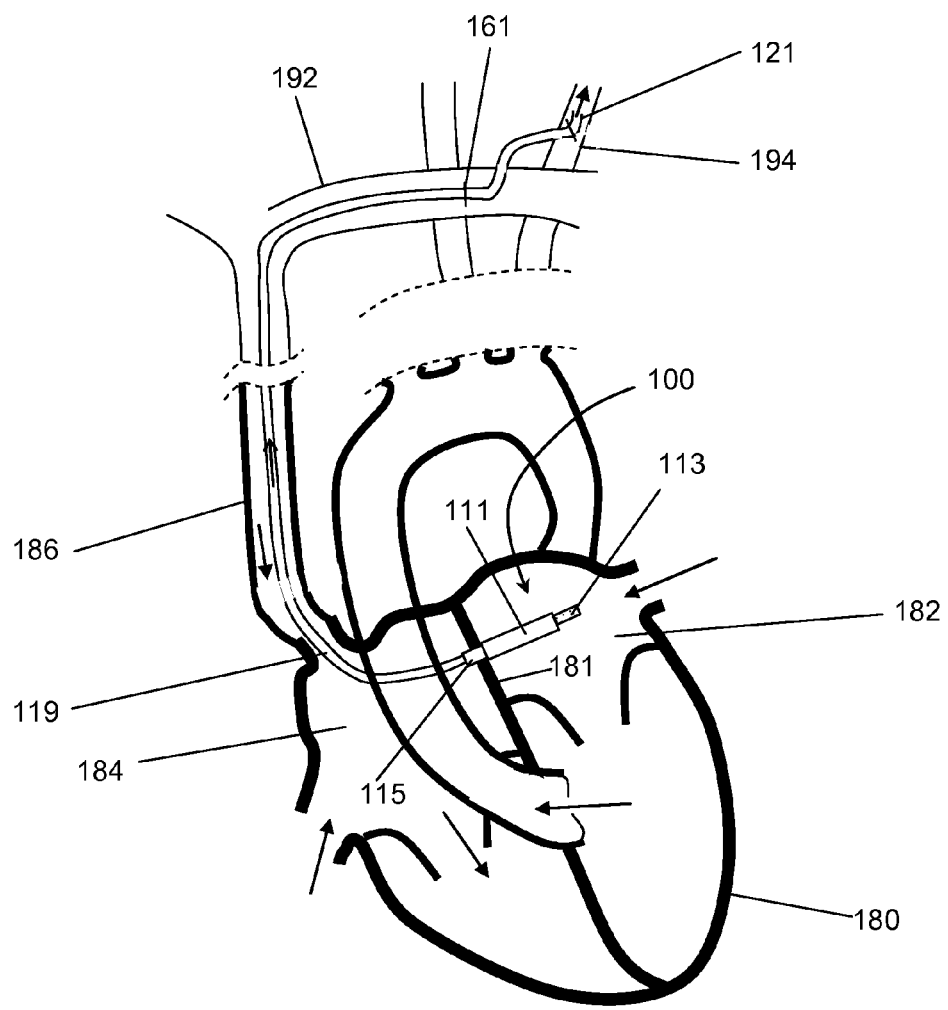
FIG. 1 illustrates an embodiment of a ventricular assist device (VAD) implanted in a heart.

Certain terms are used throughout the following description and claims to refer to particular system components. This document does not intend to distinguish between components that differ in name but not function. In the following discussion and in the claims, the terms "including" and "comprising" are used in an open-ended fashion, and thus should be interpreted to mean "including, but not limited to . . . ."

The term "continuous flow pump" is used to describe any pump which utilizes a rapidly spinning impeller or similar component to generate flow.

DETAILED DESCRIPTION OF THE PREFERRED EMBODIMENTS

VADs can be right VADs ("RVADs"), left VADs ("LVADs"), or both left and right VADs ("BiVADs") depending on which ventricle the VAD is designed to assist. In the past, LVAD's have been based on a pulsatile system in an effort to mimic the human heart. In recent years, research has focused on continuous flow systems as an alternative to the traditional pulsatile model. In a continuous flow system, blood is continuously pumped through the body rather than pulsing the blood rhythmically as in the human heart.

Continuous flow systems offer several advantages over pulsatile systems. First, continuous flow pumps are generally smaller than pulsatile pumps. Shrinking the size of artificial heart devices will allow doctors to treat women and small children who previously were not candidates for pulsatile LVADs. Second, continuous flow pumps consume less energy than pulsatile systems. This property is important for quality of life issues, allowing the device to run on smaller batteries. Finally, continuous flow pumps are mechanically much simpler; and have no flexible membranes or valves resulting in substantially improved endurance.

The field of LVADs is advancing rapidly. Like any new technology, results are improving with better device designs and increased experience. It is now becoming increasingly clear that in many patients, a pump with a rate 2 or 3 liters per minute may be of value in patients in whom early (class III) heart failure is present. By implanting such an assist device earlier in the course of the affliction, progression to class IV may be averted. Furthermore, in these earlier stage patients, it is quite probable that 2 or 3 liters of blood flow per minute may be all that is required to restore the patients to class I status.

If it is contemplated that pumps be placed in patients earlier in the course of their illness, it is imperative that it be done in a manner that minimizes invasiveness. As these patients are in no immediate peril, and can be managed for a time on medical therapy, a pump implantation procedure, if it is to be widely accepted and practiced, must be associated with relatively little morbidity and mortality.

To treat congestive failure and prevent, and possibly reverse, progression of cardiac derangements, a device needs to remove blood from the left side of the heart and deliver it into the systemic circulation in sufficient volumes that cardiac output is maintained or increased while left ventricular wall tension and work is decreased. One means is to introduce a cannula through the systemic veins, either subclavian, jugular, or femoral, and using conventional wire skills, position the tip across the atrial septum in the left atrium. Oxygenated blood removed from the left atrium through this cannula can then be returned by way of a cannula or graft attached to any systemic artery.

Figure 2:
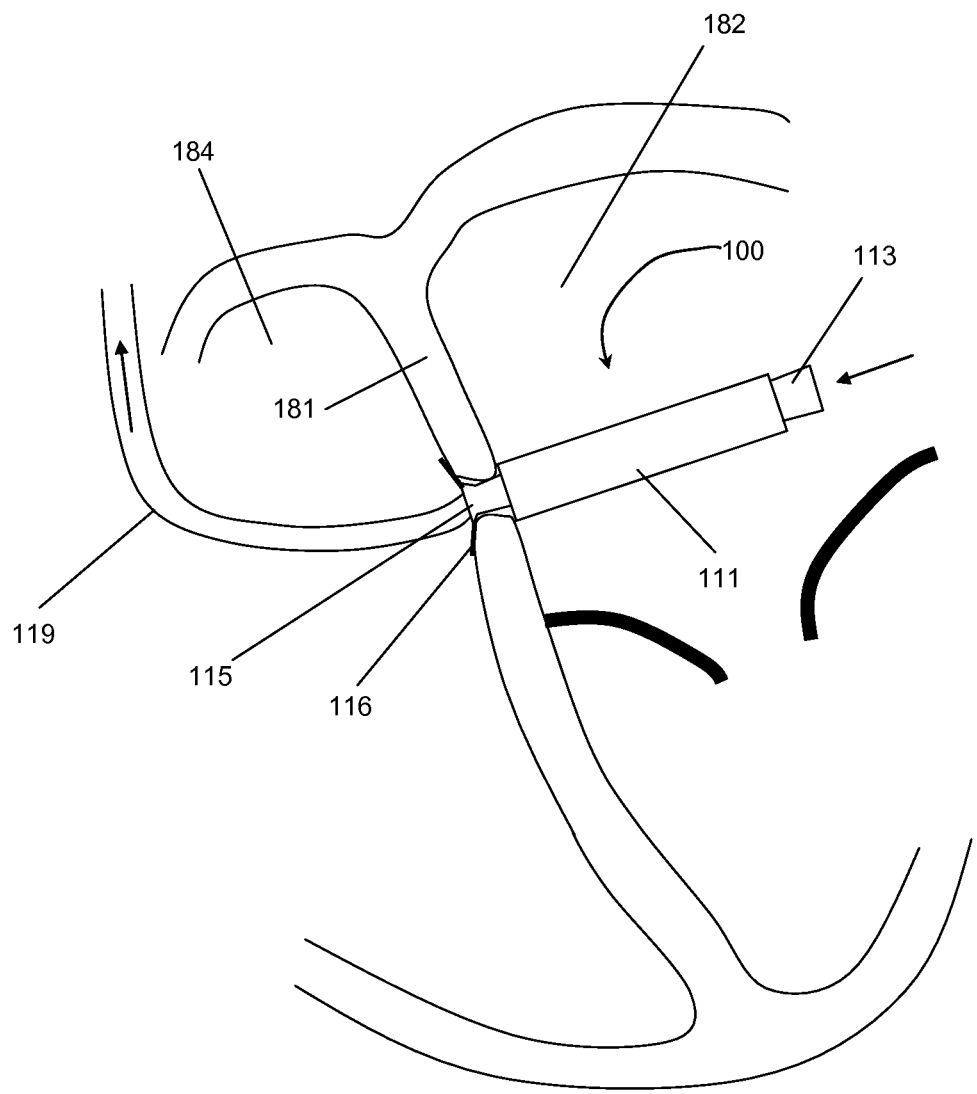
FIG. 2 illustrates a close-up of an embodiment of a VAD in the left atrium of a heart.

FIGS. 1 and 2 illustrate an embodiment of a device 100 configured specifically for limited access implantation without the need for cardiopulmonary bypass. In an embodiment, the device comprises a pump 111 adapted to be implanted within a heart atrium 182. Pump 111 has an inlet 113 and an outlet 115. A flexible conduit 119 may be coupled to the pump outlet. In addition, pump 111 has an expandable attachment collar 116 for attachment to the atrial septum 181 as shown in FIG. 2.

FIG. 1 also illustrates the configuration of an embodiment of the device as implanted within a human heart 180. Pump 111 may be attached to the wall or septum 181 dividing the right atrium 184 and left atrium 182 of the heart 180. Pump inlet 113 preferably is directed toward the center of the left atrium 182. Fresh oxygenated blood from the lungs enters the left atrium 182 and a portion may be sucked into the pump 111. Flexible outflow conduit 119 may pass interatrially through the septum 181 into the right atrium 184, up the superior vena cava 186, into the subclavian 192 vein or the ipsilateral jugular vein and through the subclavian vein or jugular vein wall 161. Preferably, flexible outflow conduit has a diameter no more than 9 mm and comprises a polymer of polyurethaneurea, polytetrafluoroethylene, polyethylene, polycarbonate, silicone, or combinations thereof. The proximal end 121 of conduit 119 may be anastomosed to the subclavian artery 194 or other suitable artery. Accordingly, the oxygenated blood from the left atrium 182 is sucked into pump and forced through conduit 119 into the subclavian artery 194 for recirculation of oxygenated blood to the body. In relation to the superior vena cava, the flow in the conduit is countercurrent. Preferably, the pump 111 comprises pressure sensitive impellers. The impellers preferably comprise angled vanes, curved vanes, flexible vanes, tapered vanes, round vanes, propellers, open impellers, closed impellers, or any combination thereof.

Preferably, the pump 111 comprises a continuous flow pump. The pump 111 itself can be any one of a variety of designs, including without limitation, centrifugal, diagonal, or axial, and the external diameter of the pump, inclusive of the motor, preferably fits through a narrow sheath such as without limitation, a 24-French sheath. The pump 111 preferably provides 2-3 liters per minute of flow. The outlet 115 of the pump 111 may be a 7 or 8 mm graft of PTFE, Dacron, or other suitable material. The electrical driveline (not shown) of the pump 111 will preferably run in or closely adjacent to the outer wall of the outflow graft.

Figure 3:
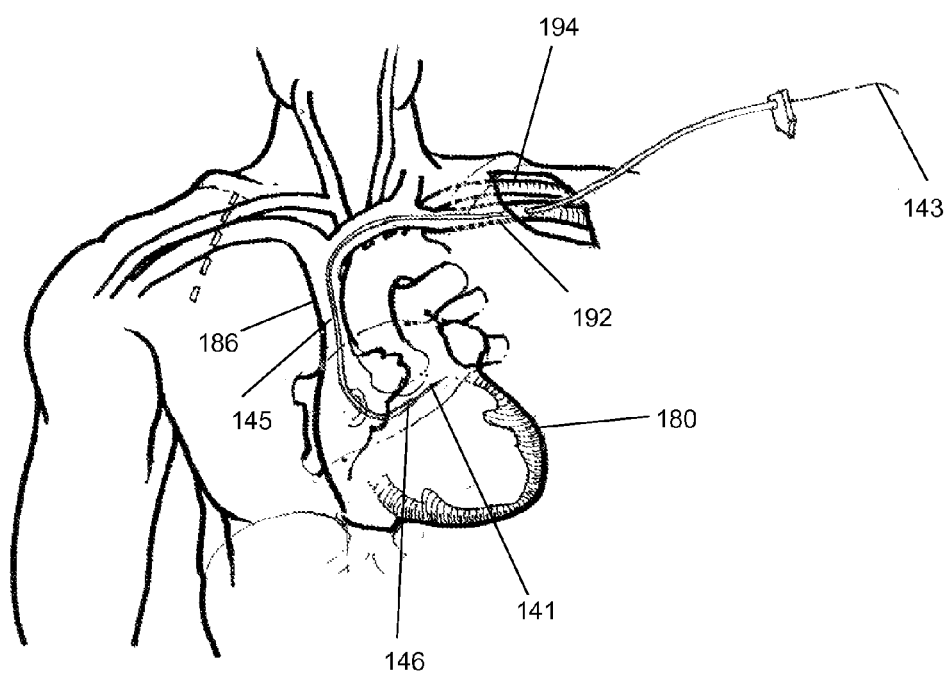
FIG. 3 illustrates an embodiment of a method of implanting the disclosed VAD in a heart.

In an embodiment of a method of assisting ventricular function of a heart, the disclosed device 100 may be implanted within a patient using novel surgical techniques as shown in FIGS. 2 and 3. More particularly, to implant embodiments of the device, a small incision may be made below the middle third of the clavicle. The subclavian artery 194 is identified and exposed, preferably on the left. A needle 141 is then introduced into the subclavian vein 192 or ipsilateral jugular vein, and a guide wire 143 is passed into the right atrium under fluoroscopic guidance. Catheters and surgical techniques may then be used to perform puncture of the atrial septum 181 and create guide wire access to the left atrium 182. A sheath 145 (e.g. thin-walled split-away 24-French sheath) may then be introduced into the left atrium 182 over a very flexible dilator that, despite flexibility, has adequate column stiffness to allow advancement. Fluoroscopy may be used to insure that the distal tip 146 of the sheath 145 is across the atrial septum 181. Alternatively, intravascular ultrasound may be used, the two imaging techniques may be used together, or other imaging modalities may be employed including but not limited to MRI, CT, and ultrasound.

Once in position, the dilator is removed and the pump 111 is placed down the sheath lumen, until the pump 111 itself is in the left atrium 182 with the inlet 113 projecting toward the center of the chamber. In one embodiment, a collar extending from the pump body that is constrained by the sheath is allowed to expand in the left atrium 182, which allows the pump 111 to be pulled back snuggly against the interatrial septum 181, minimizing hardware in the left atrium 182. In other embodiments, the collar is expanded by balloon catheter inflation, by pulling a suture, or by another mechanism.

To facilitate advancing the pump 111 down the sheath, an obturator may be placed down the lumen of the outflow graft. The obturator is preferably flexible to allow the pump 111 and outflow graft or conduit 119 to successfully navigate the sheath 145, but has sufficient column strength to allow advancement.

Once the pump 111 is in the left atrium 182, the sheath 145 is removed by splitting while using fluoroscopy to insure that the pump 111 does not dislodge. Once the sheath has been removed completely from the subclavian vein, the outflow graft and the pump driveline exits through the previously created venotomy in the ipsilateral subclavian or jugular vein. The outflow graft may be sutured the venotomy margin to prevent venous hemorrhage around the outflow graft. The distal end of the graft is beveled and sutured to the subclavian artery to deliver the blood flowing from pump 111 to the systemic circulation. The driveline is tunneled through the subcutaneous tissue to an appropriate site where it exits through the skin, and is attached to the power supply. Preferably, the outflow conduit passes retrograde through a lumen of systemic veins and exits through a wall of the systemic veins to allow the outflow conduit to be sutured, in an end-to-side fashion, to a systemic artery.

The device 100 and technique for implantation described here have several unique advantages. By positioning the pump 111 in the left atrium 182, the need for a pump pocket is eliminated, thereby reducing the likelihood of pump infection. Furthermore, the technique described above can be done without opening the chest, through a superficial incision, and does not require cardiopulmonary bypass. As the pump 111 is pulled flush against the left side of the atrial septum 181, the amount of material protruding into the left atrium 182 is minimized. This geometric arrangement also reduces the length of the pump blood path, which extends from the atrial septum 181 to the left subclavian artery, and facilitates a non-kinking lay of the outflow graft. By placing the pump 111 directly in the left atrium 182, it is possible that the likelihood of thrombus formation will be less due to high velocity flow entering the pump 111. As the outflow graft will come off the back of the pump 111 in a linear coaxial geometry, obtaining acceptable pump and graft lie should be facilitated. Although the patient may develop narrowing or even occlusion of the subclavian or jugular vein, this is generally well tolerated, and it is possible that outflow grafts of appropriate size or composed of appropriate material on the external surface may minimize this occurrence.

Figure 4:
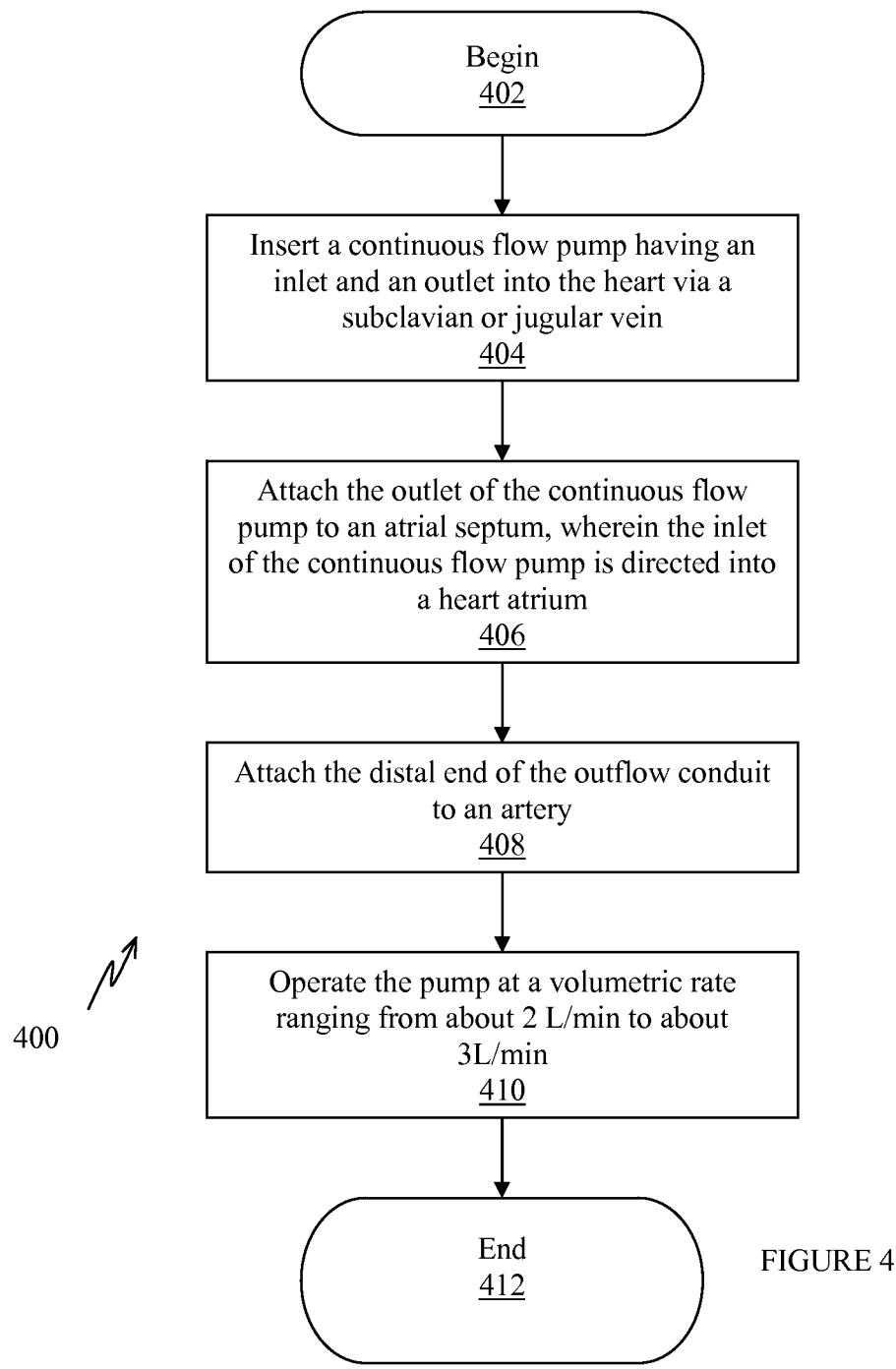
FIG. 4 illustrates a method of assisting ventricular function of a heart of a patient.

FIG. 4 illustrates a method 400 of assisting ventricular function of a heart of a patient beginning at 402 and ending at 412. At 404, a continuous flow pump having an inlet and an outlet is inserted into the heart via a subclavian or jugular vein. At 406, the outlet of the continuous flow pump is attached to an atrial septum, wherein the inlet of the continuous flow pump is directed into a heart atrium. At 408, the distal end of the outflow conduit is attached to an artery. At 410, the pump is operated at a volumetric rate ranging from about 2 L/min to about 3 L/min.

Figure 5:
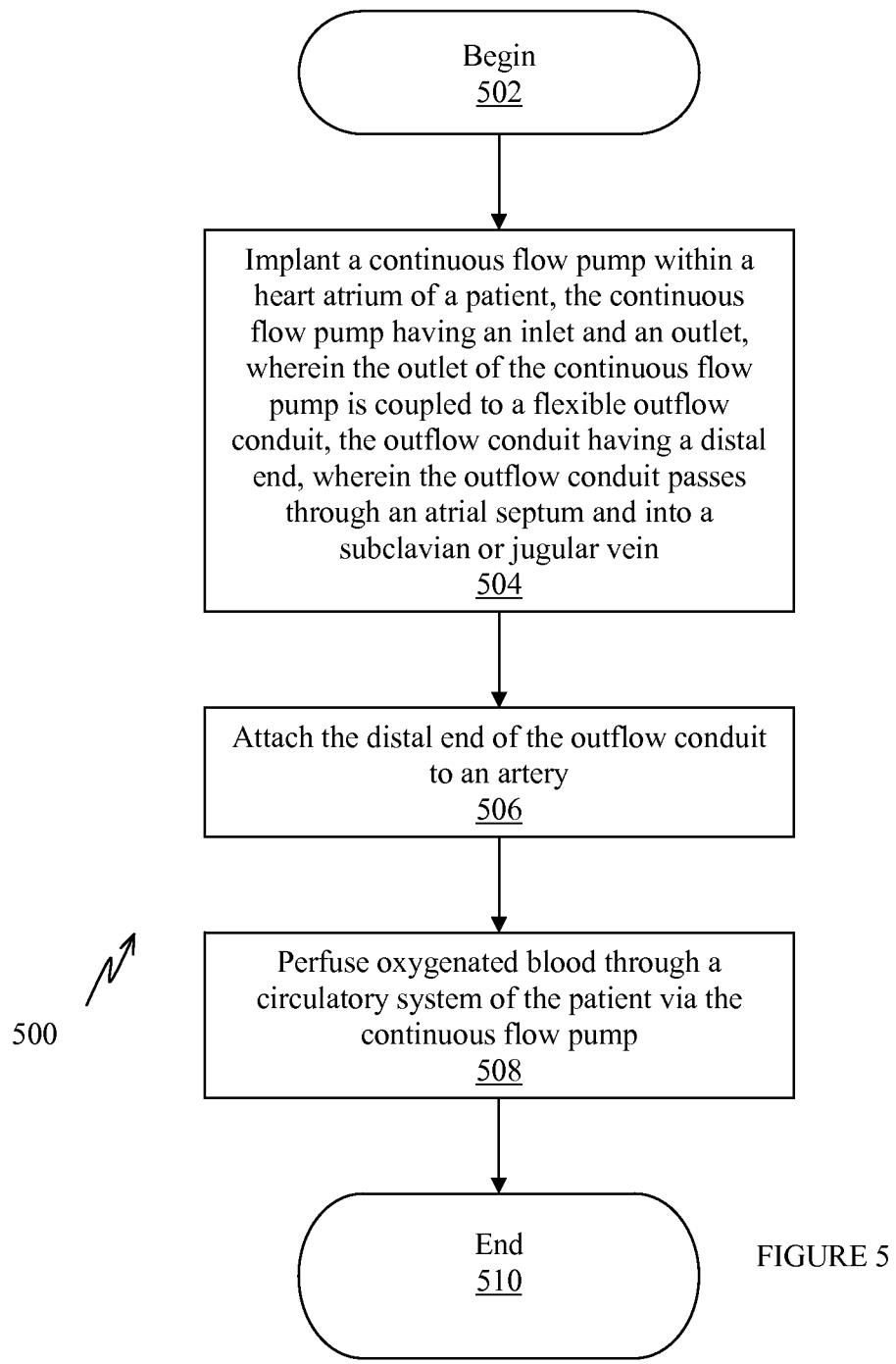
FIG. 5 illustrates a method of assisting ventricular function of a heart.

FIG. 5 illustrates a method 500 of assisting ventricular function of a heart beginning at 502 and ending at 510. At 504, a continuous flow pump is implanted within a heart atrium of a patient, the continuous flow pump having an inlet and an outlet, wherein the outlet of the continuous flow pump is coupled to a flexible outflow conduit, the outflow conduit having a distal end, wherein the outflow conduit passes through an atrial septum and into a subclavian or jugular vein. At 506, the distal end of the outflow conduit is attached to an artery. At 508, oxygenated blood is perfused through a circulatory system of the patient via the continuous flow pump.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference in the Description of the Related Art is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A medical device comprising:
    a continuous flow pump configured to fit across an atrial septal wall separating a left atrial chamber from a right atrial chamber of a heart, said pump comprising an inlet configured to be positioned in the left atrial chamber and an outlet configured to be positioned in the right atrial chamber, the pump also comprising an expandable collar to secure the pump to the atrial septal wall; and
    a flexible outflow conduit coupled to said outlet, said outflow conduit having a diameter of no more than 9 mm and configured to be contained within and extend from the right atrium and coaxially through the superior vena cava and subclavian vein and into the subclavian artery;
    wherein said pump pumps oxygenated blood from the left atrium through the outflow conduit in a direction in the superior vena cava counter to the direction of deoxygenated blood in the superior vena cava returning to the heart.

* * * * *